(12) United States Patent
Flohr et al.

(10) Patent No.: US 7,583,785 B2
(45) Date of Patent: Sep. 1, 2009

(54) DETECTING APPARATUS AND METHOD FOR DETECTING AN OBJECT BY MEANS OF A PROJECTION THROUGH THE OBJECT BY MEANS OF X-RAYS, AND A CONTRAST—AND NOISE-OPTIMIZED QUANTUM COUNTING DETECTOR

(75) Inventors: Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 153 days.

(21) Appl. No.: 11/806,160

(22) Filed: May 30, 2007

(65) Prior Publication Data

US 2008/0001093 A1    Jan. 3, 2008

(30) Foreign Application Priority Data

May 31, 2006    (DE) ................... 10 2006 025 401

(51) Int. Cl.
*G01N 23/00*    (2006.01)
(52) U.S. Cl. ............................................ 378/19; 378/4
(58) Field of Classification Search ................ 378/4–20
See application file for complete search history.

(56) References Cited

U.S. PATENT DOCUMENTS 7,139,362 B2    11/2006    Heismann et al.
7,193,217 B2    3/2007    Heismann et al.
2006/0086913 A1    4/2006    Spahn
2006/0109949 A1*    5/2006    Tkaczyk et al. ................. 378/4
2006/0280281 A1*    12/2006    Flohr et al. ..................... 378/5

FOREIGN PATENT DOCUMENTS

DE        1021638 A1    10/2003
DE        10307752 A1    8/2004
DE    102004048962 A1    4/2006
DE    102006006411 A1    8/2007

* cited by examiner

*Primary Examiner*—Hoon Song
(74) *Attorney, Agent, or Firm*—Harness, Dickey & Pierce, P.L.C.

(57) ABSTRACT

A detecting apparatus is disclosed for detecting an object by way of a projection through the object onto a detection plane. In at least one embodiment, the detecting apparatus has a transmitter that is designed to emit quanta. In at least one embodiment the detection apparatus also has a detector, arranged in a detection plane, for detecting the emitted quanta, the detector being designed and arranged to generate at least one detector signal at least partially representing the object in a projection, as a function of the quanta received through the object. In at least one embodiment, the detecting apparatus is designed to generate as a function of the generated detector signal for a detected quantum a quantum signal that represents the quantum energy of one detected quantum. Finally, in at least one embodiment the detecting apparatus is designed to generate a sum signal that corresponds to a sum of the quantum energies of the quantum energies represented by the quantum signals.

13 Claims, 1 Drawing Sheet

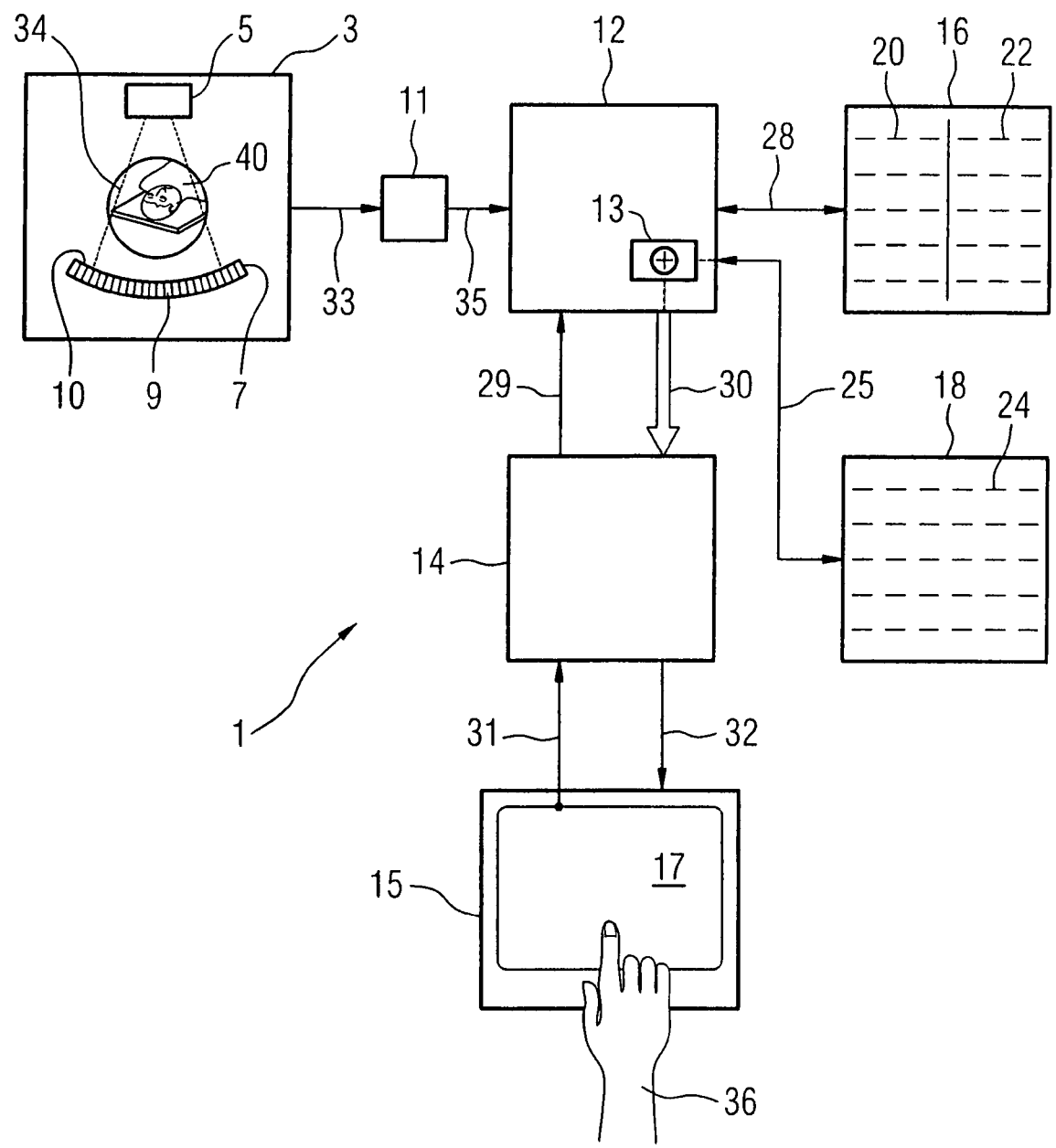

DETECTING APPARATUS AND METHOD FOR DETECTING AN OBJECT BY MEANS OF A PROJECTION THROUGH THE OBJECT BY MEANS OF X-RAYS, AND A CONTRAST—AND NOISE-OPTIMIZED QUANTUM COUNTING DETECTOR

PRIORITY STATEMENT

The present application hereby claims priority under 35 U.S.C. §119 on German patent application number DE 10 2006 025 401.5 filed May 31, 2006, the entire contents of which is hereby incorporated herein by reference.

FIELD

Embodiments of the invention generally relate to a detecting apparatus for detecting an object, such as by use of a projection through the object onto a projection plane for example.

BACKGROUND

In the case of known detecting apparatuses, in particular of computer tomographs, the problem arises that noise in a detector output signal of a detector for detecting X-radiation projected through an object exhibits such a noise that weak contrasts can be represented only with difficulty or not at all any longer in a detection result produced in such a way.

SUMMARY

In at least one embodiment, the present invention includes a detecting apparatus that improves upon and/or does not exhibit at least one of the above-named problems.

A detecting apparatus of at least one embodiment includes a transmitter that is designed to emit quanta. The detecting apparatus also has a detector, arranged in a detection plane, for detecting the emitted quanta, the detector being designed and arranged to generate at least one detector signal at least partially representing the object in a projection, as a function of the quanta received through the object. The detecting apparatus is designed to generate as a function of the generated detector signal for a detected quantum a quantum signal that represents the quantum energy of one detected quantum. The detecting apparatus is preferably designed to generate a sum signal that corresponds to a sum of the quantum energies of the quantum energies represented by the quantum signals.

In order to generate the quantum signal as a function of the generated detector signal, the detecting apparatus may have, in at least one embodiment, a quantum separator, in particular with fast detection electronics.

A noise of a detector output signal can advantageously be reduced by generating a quantum signal for a quantum detected by the detector, in particular for each quantum detected by the detector. It is further advantageously possible to attain a weighting optimized for all energies by summing up the quantum energies represented by the quantum signals and generating a sum signal.

In an example embodiment, the detector includes a multiplicity of detector matrix elements that are respectively designed to detect quanta, in particular X-ray quanta, and to generate a detector output signal representing the object at least partially, as a function of the detected quanta.

The detector matrix elements can, for example, include semiconductor detectors that select quanta, in particular semiconductor detectors with gadolinium, or with mercury iodide or with gadolinium telluride or gadolinium zinc telluride or a combination of these.

In an example embodiment, the detecting apparatus includes at least one weighting discriminator connected at least indirectly to the detector. The weighting discriminator is designed to generate the quantum signal, or a data record corresponding to the quantum signal, in accordance with a predetermined assignment rule.

Each quantum can advantageously be assigned a discrete quantum energy by the weighting discriminator.

In a further example embodiment, the weighting discriminator has a memory with a lookup table stored in the memory. The lookup table has a multiplicity of assignments of detector signal values and quantum signal values to be assigned to the detector signal values.

An assignment can represent a predetermined assignment rule or a weighting, in particular a weighting function. For example, a weighting function can allocate a predetermined value for each detected quantum such that the weighting function forms a threshold value discriminator. An assignment can be performed linearly or nonlinearly as a function of the quantum energies.

For example, detected quanta can no longer be assigned with a quantum energy below or above a predetermined limit value, or can be assigned with a predetermined weighting factor in accordance with the predetermined assignment rule.

The weighting discriminator is designed in this embodiment to determine a detector signal value corresponding to a detector signal from the lookup table stored in the memory, and to assign a quantum energy value assigned to the detector signal value in accordance with the lookup table. Furthermore, the weighting discriminator is designed to generate a quantum signal representing the assigned quantum energy value, and to output said quantum signal on the output side. The predetermined assignment rule is therefore already implemented in the lookup table.

In an example design variant, the weighting discriminator is designed to generate the quantum signal in accordance with the predetermined assignment rule by assignment to discrete quantum energy values. In this embodiment, the quantum signal represents discrete quantum energy values.

A quantum signal can be implemented by a quantum signal data record that represents a quantum energy of a detected quantum. A sum signal can be implemented by a sum signal data record that corresponds to a sum of the quantum energies of the quantum energies represented by the quantum signals.

Furthermore, the weighting discriminator can preferably be designed to generate the quantum signal by way of fuzzy discrimination, in this embodiment the weighting discriminator having a fuzzy unit that can generate the quantum signal as a function of fuzzy input parameters, in particular of detector signals.

A noise of the detector signal can advantageously be reduced by the assignment of discrete quantum energy values to a detector signal.

In an advantageous embodiment, the weighting discriminator can generate the quantum signal as a function of a probability or of a probability density.

In an advantageous embodiment, the detecting apparatus has a buffer memory, connected at least indirectly to the weighting discriminator, for quantum energy data records, the quantum energy data records respectively representing a quantum energy of quanta received successively over time.

In this embodiment, the weighting discriminator is preferably designed to assess in accordance with a predetermined distribution function quantum energies, held available in the buffer memory, of individual received quanta in accordance with a predetermined distribution function, and to generate a quantum signal that represents the result of assessment in accordance with the predetermined distribution function.

The predetermined distribution function can supply a probability or a probability density as result.

For example, a predetermined distribution function can be a normal distribution function or a Poisson distribution function. The weighting discriminator can be designed in such a way that the quantum signal is generated as a function of the predetermined distribution function and as a function of an expectation and/or a standard deviation or a variance.

At least one embodiment of the invention also relates to a computer tomograph having a detecting apparatus, the computer tomograph being designed to generate a 2D data record that represents the sum signals for each detector matrix element and that is designed to generate from the 2D data records, in particular by backprojection, a 3D data record that represents the object in three dimensions.

The 2D data records respectively represent a projection of the object onto a detection plane in two dimensions.

A computer tomograph of the type designated above can advantageously generate a 3D data record which represents the object in three dimensions with low noise.

A detection plane can be flat or curved, and in the case of a curved detection plane a detection plane can form a section of a cylinder wall. The detector matrix elements can be arranged in the detection plane.

At least one embodiment of the invention also relates to a method for detecting an object by use of a projection through the object onto a detection plane, wherein at least one quantum is transmitted through the object;
the quantum is received and a reception signal representing the object is generated; and
a quantum signal representing the quantum energy of the reception signal is generated.

The method, in at least one embodiment, can advantageously have the step that a sum signal that represents the sum of the quantum energies of the quantum signals is generated, in particular by summing or integration.

BRIEF DESCRIPTION OF THE DRAWINGS

An example embodiment of the invention is now explained below with the aid of a FIGURE.

The FIGURE shows an example embodiment for a detecting apparatus for detecting an object by way of a projection of X-rays through the object onto the detection plane.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

The FIGURE shows an example embodiment for an arrangement 1 for detecting an object 40 in three dimensions.

The arrangement 1 has a detecting apparatus 3. The arrangement 1 or the detecting apparatus 3, or both, can be a component of a computer tomograph.

The detecting apparatus 3 has a transmitter 5 for emitting at least one X-ray quantum 34. The detecting apparatus 3 also has a detector 7 arranged in a detection plane 10. The detector 7 has a multiplicity of detector matrix elements of which the detector matrix element 9 is designated by way of example.

The detector matrix elements 9 are respectively designed and arranged to generate a detector signal at least partially representing the object 40 in a projection, as a function of the at least one quantum 34 received through the object 40.

The arrangement 1 has a quantum separator 11 that is designed to generate at least one quantum signal as a function of a detector signal received on the input side, a quantum signal representing a quantum energy of the received quantum 34. The quantum separator 11 is at least indirectly connected to the detector 7.

In order to generate the quantum signal, the quantum separator 11 can have fast detecting electronics that is designed to scan the detector signal at a scanning rate in the range of picoseconds, preferably at a scanning rate of less than 100 picoseconds, further preferably less than 10 picoseconds, with particular preference less than one picosecond, and thus to detect at least one signal component of the detector signal that corresponds to a received quantum.

For example, the quantum separator 11 is designed to separate individual quanta from a detector signal that has a quantum density of $10^9$ quanta per second and square millimeter.

The quantum separator 11 is connected on the input side via a connecting line 35 to the detecting apparatus 3, and at least indirectly there to the detector 7.

The arrangement 1 also has a weighting discriminator 12, an image processing apparatus 14, an image reproduction unit 15, a lookup memory 16 and a buffer memory 18.

The weighting discriminator 12 is designed to generate the quantum signal in accordance with a predetermined assignment rule.

In this example embodiment, the weighting discriminator 12 can generate the quantum signal in accordance with the predetermined assignment rule by assignment to discrete quantum energy values.

For this purpose, the weighting discriminator 12 is connected to the lookup memory 16 via a connecting line 28. Quantum energy data records and detector signal data records are stored in the lookup memory 16.

The detector signal data record 20 and the quantum energy data record 22 are designated by way of example. The detector signal data record 20 corresponds to a received quantum, and represents, for example, a detector signal amplitude, a detector signal frequency or a detector signal half value width of a detector signal pulse, or a combination of these. The quantum energy data record 22 represents a discrete energy of a quantum, in particular an X-ray quantum.

Via the connecting line 28, the weighting discriminator 12 can access the lookup memory 16 and read out detector signal data records 20 and quantum energy data records 22 stored there, and determine from the detector signal data records 20 a detector signal data record that corresponds to the detector signal received on the input side via the connecting line 35. The weighting discriminator 12 can then generate a quantum signal that represents a discrete quantum energy of a quantum energy data record 22 that corresponds to the previously determined detector signal data record 20.

The weighting discriminator 12 is designed to generate from the quantum signal a quantum energy data record 24, and to transmit the latter via the connecting line 25 to the buffer memory 18 and store it there. Thus, quantum energy data records 24 succeeding one another over time are stored in the buffer memory 18 for each detector matrix element 9 in the course of a detection process by the detector 7.

The weighting discriminator 12 can be designed to add to one another quantum energy data records 24 that succeed one another over time and respectively correspond to exactly one detector matrix element 9, and to generate a sum signal that represents the sum of the quantum energies represented by the quantum energy data records.

In order to add up the quantum energies as described above, the arrangement 1 can have a summer 13 that can be a component of the weighting discriminator 12, or can be connected at least indirectly to the weighting discriminator 12. In this exemplary embodiment, the summer 13 is a component of the weighting discriminator 12 and is—as illustrated by dashes— connected on the input side to the buffer memory 18, and on the output side to the data bus 30.

In addition to, or independently of the abovedescribed properties of the weighting discriminator 12, the weighting discriminator 12 can be designed to assess in accordance with a predetermined distribution function quantum energies, held available in the buffer memory 18, of individual received quanta, and to generate a quantum signal that represents the result of assessment in accordance with the predetermined distribution function. Such a predetermined distribution function can be, for example, a Poisson distribution function.

The quantum signal can, for example, be generated as a function of a variance of the quantum energies represented by the quantum energy data records 24, referred to a mean quantum energy value.

The weighting discriminator 12 is connected on the output side to the image processing apparatus 14 via a data bus 30, and it is designed to output the quantum signal and/or the sum signal on the output side. The quantum signal and/or the sum signal represent the object 40 detected by the detecting apparatus 3 in a projection in two dimensions. The quantum signal and/or the sum signal can be represented by a 2D data record.

The image processing apparatus 14 is designed to generate in particular by means of backprojection, from the 2D data records received on the input side via the data bus 30, or from the sum signal, a 3D data record that represents the object 40 in three dimensions.

In this embodiment, the 3D data record can be formed by a multiplicity of voxel object points that together represent the object 40 at least partially in three dimensions.

The image processing apparatus 14 is connected to the image reproduction unit 15 via a connecting line 32. The image processing apparatus 14 is designed to output the 3D data record on the output side via the connecting line 32 for the purpose of reproduction by way of the image reproduction unit 15.

The image reproduction unit 15 has a touch-sensitive surface 17 that is connected to the image processing apparatus 14 via a connecting line 31. The touch-sensitive surface is designed to generate as a function of touching of the touch-sensitive surface 17 a touch signal that represents a touch location of the touch-sensitive surface 17, and to output it on the output side.

Also illustrated is a hand of a user 34 that can, for example, indirectly generate the touch signal by touching the touch-sensitive surface 17. For example, the image processing apparatus 14 can generate the 3D data record as a function of a user interaction signal, in particular the touch signal.

The image processing apparatus 14 is connected to the weighting discriminator 12 via a connecting line 29. The image processing apparatus 14 can output the touch signal received on the input side via the connecting line 31 to the weighting discriminator 12 via the connecting line 29.

For example, the weighting discriminator 12 can have at least two, or a number of predetermined assignment rules for generating a quantum signal as a function of a detector signal.

Furthermore, the weighting discriminator 12 can, for example, be designed to select a predetermined assignment rule for generating the quantum signal and/or a predetermined distribution function for generating a quantum signal and/or sum signal, as a function of a user interaction signal, in particular the touch signal received via the connecting line 29.

Further advantageous embodiments follow from the features described in the dependent claims, and from a combination of the features described in the dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detecting apparatus for detecting an object by way of a projection through the object onto a detection plane, comprising:
    a transmitter to emit quanta; and
    at least one detector, arranged in a detection plane to receive the emitted quanta, to generate at least one detector signal representing at least partially the object in a projection, as a function of the quanta received through the object, the detecting apparatus being designed to generate, as a function of the generated detector signal for a detected quantum, a quantum signal that represents the quantum energy of one detected quantum, wherein the detecting apparatus includes at least one weighting discriminator, at least indirectly connected to the detector, the weighting discriminator being configured to generate the quantum signal in accordance with a predetermined assignment rule and further configured to generate the quantum signal by fuzzy discrimination as a function of fuzzy input parameters, the fuzzy input parameters including detector signals.

2. The detecting apparatus as claimed in claim 1, wherein the at least one weighting discriminator is designed to generate the quantum signal in accordance with the predetermined assignment rule by assignment to discrete quantum energy values.

3. The detecting apparatus as claimed in claim 1, wherein the detecting apparatus includes a buffer memory for quantum energy data records, connected at least indirectly to the weighting discriminator, the quantum energy data records respectively representing a quantum energy of quanta received successively over time, and the weighting discriminator being designed to assess in accordance with a predetermined distribution function quantum energies, held available in the buffer memory, of individual received quanta, and to generate a quantum signal that represents the result of assessment in accordance with the predetermined distribution function.

4. The detecting apparatus as claimed in claim 3, wherein the predetermined distribution function includes at least one of a normal distribution function and a Poisson distribution function.

5. The detecting apparatus as claimed in claim 1, wherein the detector includes a multiplicity of detector matrix elements, respectively designed to generate a detector signal as a function of a received quantum.

6. The detecting apparatus as claimed in claim 5, wherein the detector matrix elements include quantum counting semiconductor detectors.

7. A computer tomograph, comprising a detecting apparatus as claimed in claim 6, the computer tomograph being designed to generate a 2D data record that represents the sum signals or the quantum signals for each detector matrix element and to generate from the 2D data records, which respectively represent a projection of the object onto the detection plane, a 3D data record that represents the object in three dimensions.

8. A computer tomograph, comprising a detecting apparatus as claimed in claim 5, the computer tomograph being designed to generate a 2D data record that represents the sum signals or the quantum signals for each detector matrix element and to generate from the 2D data records, which respectively represent a projection of the object onto the detection plane, a 3D data record that represents the object in three dimensions.

9. A computer tomograph, comprising a detecting apparatus as claimed in claim 1, the computer tomograph being designed to generate a 2D data record that represents the sum signals or the quantum signals for each detector matrix element and to generate from the 2D data records, which respectively represent a projection of the object onto the detection plane, a 3D data record that represents the object in three dimensions.

10. A method for detecting an object by way of a projection through the object onto a detection plane, the method comprising:
    transmitting at least one quantum through the object;
    generating, from the received quantum, a reception signal representing the object; and
    generating a quantum signal representing the quantum energy of the reception signal, wherein generating the quantum signal includes generating the quantum signal in accordance with a predetermined assignment rule and by fuzzy discrimination as a function of fuzzy input parameters using a weighting discriminator included in a detecting apparatus, the fuzzy input parameters including detector signals.

11. A computer readable medium including program segments for, when executed on a computer device, causing the computer device to implement the method of claim 10.

12. A detecting apparatus for detecting an object by way of a projection through the object onto a detection plane, comprising:
    a transmitter to emit quanta;
    at least one detector, arranged in a detection plane to receive the emitted quanta, to generate at least one detector signal representing at least partially the object in a projection, as a function of the quanta received through the object;

means for generating, as a function of the generated detector signal for a detected quantum, a quantum signal that represents the quantum energy of one detected quantum; and wherein the detecting apparatus includes at least one weighting discrimination means, at least indirectly connected to the detector, the weighting discrimination means being configured to generate the quantum signal in accordance with a predetermined assignment rule and further configured to generate the quantum signal by fuzzy discrimination as a function of fuzzy input parameters, the fuzzy input parameters including detector signals.

13. A computer tomograph, comprising a detecting apparatus as claimed in claim 12, the computer tomograph being designed to generate a 2D data record that represents the sum signals or the quantum signals for each detector matrix element and to generate from the 2D data records, which respectively represent a projection of the object onto the detection plane, a 3D data record that represents the object in three dimensions.

* * * * *